(12) United States Patent
Humphreys

(10) Patent No.: US 8,053,562 B2
(45) Date of Patent: Nov. 8, 2011

(54) MODIFIED ANTIBODY FRAGMENTS

(75) Inventor: David Paul Humphreys, Slough (GB)

(73) Assignee: UCB Pharma S.A., Brussels (BE)

( * ) Notice: Subject to any disclaimer, the term of this patent is extended or adjusted under 35 U.S.C. 154(b) by 658 days.

(21) Appl. No.: 11/995,740

(22) PCT Filed: Jul. 17, 2006

(86) PCT No.: PCT/GB2006/002649
§ 371 (c)(1),
(2), (4) Date: Jun. 16, 2008

(87) PCT Pub. No.: WO2007/010231
PCT Pub. Date: Jan. 25, 2007

(65) Prior Publication Data
US 2008/0269466 A1   Oct. 30, 2008

(30) Foreign Application Priority Data

Jul. 19, 2005   (GB) .................................. 0514779.8

(51) Int. Cl.
*C12P 21/08* (2006.01)
(52) U.S. Cl. ................................ 530/387.3; 530/391.1
(58) Field of Classification Search ............... 530/391.1, 530/387.3
See application file for complete search history.

(56) References Cited

U.S. PATENT DOCUMENTS 5,219,996 A   6/1993   Bodmer et al.
6,982,321 B2 *  1/2006   Winter ........................ 530/387.3
2003/0125232 A1 *  7/2003   Griffin et al. ..................... 514/1
2005/0244403 A1 * 11/2005   Lazar et al. ................ 424/130.1

FOREIGN PATENT DOCUMENTS

| WO | 03/080674 | 10/2003 |
|---|---|---|
| WO | 2004/044004 | 5/2004 |
| WO | 2004/074322 | 9/2004 |
| WO | WO 2004106375 A1 * | 12/2004 |
| WO | 2005/003169 | 1/2005 |
| WO | 2005/003170 | 1/2005 |
| WO | 2005/003171 | 1/2005 |
| WO | WO2006/034488 | 3/2006 |

OTHER PUBLICATIONS

Rothlisberger et al (JMB, 347-773-789, 2005).*
Poljak et al (PNAS 70(12):3305-3310, 1973).*

* cited by examiner

*Primary Examiner* — Misook Yu
*Assistant Examiner* — Brad Duffy
(74) *Attorney, Agent, or Firm* — McDonnell Boehnen Hulbert & Berghoff LLP

(57) ABSTRACT

The present invention relates to a new class of modified antibody fragments. The present invention provides an antibody fragment to which one or more effector molecules is attached characterized in that the native interchain disulphide bond between the heavy (CHI) and light (CL) chain constant regions is absent and the heavy chain (CHI) and light chain (CL) constant regions are linked by an interchain disulphide bond between a pair of engineered cysteines, one in the light chain constant (CL) region and the other in the heavy chain constant (CHI) region.

12 Claims, No Drawings

MODIFIED ANTIBODY FRAGMENTS

This is a National Stage of International Application No. PCT/GB2006/002649, filed Jul. 17, 2006.

The present invention relates to antibody fragments and more specifically provides antibody fragments to which one or more effector molecules are attached and methods for their production.

The high specificity and affinity of antibody variable regions make them ideal diagnostic and therapeutic agents, particularly for modulating protein:protein interactions. Antibody fragments are proving to be versatile therapeutic agents, as seen by the recent success of products such as ReoPro®. The targeting function encoded in Fv, Fab, Fab', F(ab)$_2$ and other antibody fragments can be used directly or can be conjugated to one or more effector molecules such as cytotoxic drugs, toxins or polymer molecules to increase efficacy. For example, since these fragments lack an Fc region they have a short circulating half-life in animals but this can be improved by conjugation to certain types of polymer such as polyethylene glycol (PEG). Increasing the size of the conjugated PEG has been shown to increase the circulating half-life from minutes to many hours and modification of a Fab' with PEG ranging from 5 kDa to 100 kDa has been demonstrated (Chapman et al., 1999, Nature Biotechnology, 17, 780-783; Leong et al., 2001, Cytokine, 16, 106-119; Chapman, 2002, Advanced Drug Delivery Reviews, 54, 531-545). PEGylated antibody fragments such as CDP870 are currently undergoing clinical trials where the effect of the conjugated PEG is to bring the circulating half-life to acceptable levels for therapy.

Effector molecules may be attached to antibody fragments by a number of different methods, including through aldehyde sugars or more commonly through any available amino acid side-chain or terminal amino acid functional group located in the antibody fragment, for example any free amino, imino, thiol, hydroxyl or carboxyl group. The site of attachment of effector molecules can be either random or site specific.

Random attachment is often achieved through amino acids such as lysine and this results in effector molecules being attached at a number of sites throughout the antibody fragment depending on the position of the lysines. While this has been successful in some cases the exact location and number of effector molecules attached cannot be controlled and this can lead to loss of activity for example if too few are attached and/or loss of affinity if for example they interfere with the antigen binding site (Chapman 2002 Advanced Drug Delivery Reviews, 54, 531-545). As a result, controlled site specific attachment of effector molecules is usually the method of choice.

Site specific attachment of effector molecules is most commonly achieved by attachment to cysteine residues since such residues are relatively uncommon in antibody fragments. Antibody hinges are popular regions for site specific attachment since these contain cysteine residues and are remote from other regions of the antibody likely to be involved in antigen binding. Suitable hinges either occur naturally in the fragment or may be created using recombinant DNA techniques (See for example U.S. Pat. No. 5,677,425; WO98/25971; Leong et al, 2001 Cytokine, 16, 106-119; Chapman et al., 1999 Nature Biotechnology, 17, 780-783). Alternatively, or in addition, site-specific cysteines may also be engineered into the antibody fragment for example to create surface exposed cysteine(s) for effector molecule attachment (U.S. Pat. No. 5,219,996).

Examples of antibody fragments have recently been described in which native and engineered cysteines are used for the site-specific attachment of effector molecules (See WO2005003169, WO2005003170 and WO2005003171). In all of these fragments the native interchain disulphide bond between the heavy and light chain constant regions ($C_H1$ and $C_L$) is absent either because the interchain cysteines have been used as a site of attachment for effector molecules or because the interchain cysteines have been replaced by another amino acid to avoid effector molecule attachment to those cysteines. These fragments may also comprise engineered cysteines for use as sites of effector molecule attachment. In one example these engineered cysteines are a pair of engineered cysteines which form a disulphide link between the heavy and light chain constant regions of the antibody fragment starting material; said disulphide linkage is lost however once effector molecules are attached to those cysteines.

The present invention provides alternative antibody fragment-effector molecule conjugates in which the heavy and light chains of the antibody fragments are linked by an engineered interchain disulphide bond which is not the native interchain disulphide bond. This engineered interchain disulphide bond is retained during effector molecule attachment even when strong reducing agents are used. The invention also provides sites in the antibody light chain:heavy chain interface where pairs of cysteines can be successfully engineered to introduce a disulphide bond that is sufficiently buried that it is largely inaccessible to reducing agents and effector molecules.

A particular advantage of these fragments lies in that the disulphide bond between the engineered interchain cysteines remains intact during effector molecule attachment.

Thus according to the present invention there is provided an antibody fragment to which one or more effector molecules is attached characterized in that the native interchain disulphide bond between the heavy ($C_H1$) and light ($C_L$) chain constant regions is absent and the heavy chain ($C_H1$) and light chain ($C_L$) constant regions are linked by an interchain disulphide bond between a pair of engineered cysteines, one in the light chain ($C_L$) constant region and the other in the heavy chain constant ($C_H1$) region.

The term 'native interchain disulphide bond' as used herein refers to the interchain disulphide bond that exists between the cysteine in the heavy and light chain constant regions encoded in a naturally occurring germline antibody gene. In particular the native interchain cysteines are a cysteine in the constant region of the light chain ($C_L$) and a cysteine in the first constant region of the heavy chain ($C_H1$) that are disulphide linked to each other in naturally occurring antibodies. Examples of such cysteines may typically be found at position 214 of the light chain and 233 of the heavy chain of human IgG1, 127 of the heavy chain of human IgM, IgE, IgG2, IgG3, IgG4 and 128 of the heavy chain of human IgD and IgA2B, as defined by Kabat et al., 1987, in Sequences of Proteins of Immunological Interest, US Department of Health and Human Services, NIH, USA. It will be appreciated that the exact positions of these cysteines may vary from that of naturally occurring antibodies if any modifications, such as deletions, insertions and/or substitutions have been made to the antibody fragment.

In the antibody fragments of the present invention the native interchain disulphide bond is absent. The native interchain disulphide bond may be absent because one or more effector molecules are attached to the interchain cysteines, see for example the fragments described in WO2005003170 and WO2005003171. Hence in one embodiment of the invention the native interchain disulphide bond is absent because an effector molecule is attached to the native interchain cysteine of $C_L$ and the native interchain cysteine of $C_H1$ in the antibody fragment. In one embodiment the interchain cysteine of $C_L$ to which an effector molecule is attached is at position 214 of the light chain and the interchain cysteine of $C_H1$ to which an effector molecule is attached is at position 233 of the heavy chain.

In another embodiment the native interchain disulphide bond is absent in the antibody fragments of the present invention because the interchain cysteines have been replaced with another amino acid, such as serine. Antibody fragments in which the native interchain cysteines have been replaced by serine have been described in WO2005003169.

In the antibody fragments of the present invention the heavy and light chain constant regions are linked by an interchain disulphide bond between an engineered cysteine in the light chain constant region ($C_L$) and an engineered cysteine in the heavy chain constant region ($C_H1$).

The term 'engineered cysteine' as used herein refers to a cysteine which has been introduced into the antibody fragment sequence at a position where a cysteine does not occur in the natural germline antibody sequence. Typically the engineered cysteine replaces another amino acid normally found at that position. The cysteines are typically engineered as a cysteine pair consisting of a cysteine in the heavy chain constant region ($C_H1$) and a cysteine in the light chain constant region ($C_L$). The cysteine pair allows a disulphide bond to be formed between the heavy and the light chain of the antibody fragment.

Suitable positions for the engineered cysteines can be determined empirically by a person skilled in the art by engineering the cysteines into the heavy and light chain constant regions and testing for the presence of a disulphide bond between the cysteines before and after effector molecule attachment using the methods described herein, such as non reducing SDS-PAGE and immunoblotting. The skilled person can identify potential sites that may be suitable for the introduction of cysteine residues using information available in the art such as antibody x-ray crystal structures combined with computer programs that predict sites for the introduction of disulphide bridges or visual inspection of the structures (See for example U.S.20030125232). Disulphide bonds have been engineered into a number of model proteins both in order to try and stabilise the protein and also in order to study the structural and neighbour requirements of cysteine amino acids if they are to form a disulphide pair (reviewed in Dani et al., Prot. Eng. 2003 v 16 p 187-193). Computer software that might be used to identify potentially useful sites for introduction of novel disulphide bond forming cysteines has also been created (Dani et al., 2003). Analysis of the reference protein dataset by Dani et al. showed that it is desirable to choose positions that are in relatively mobile regions close to the protein surface. This ensures that the protein structure can relax without incurring a significant energetic penalty. Antibody Ig fold based variants have been stabilised by the introduction of disulphide bonds most notably Fv regions as 'dsFv' (Glockshuber et al., 1990 Biochemistry 29:1362-1367), for stabilisation of leucine zipper dimerised scFv 'miniantibodies' (Pack and Pluckthun 1992 Biochemistry 31:1579-1584) and for dimerisation of scFv domains (McCartney et al., 1994 Protein Engineering 8: 301-304). The CH3 domain of IgG Fc region has also had cysteines introduced at 6 positions in order to aid in desired Fc heterodimerisation (Merchant et al., 1998 Nature Biotech. 16:677-681).

The physical properties of native disulphides have been described in detail (Petersen et al., Prot. Eng 1999 v12 p 535-548) and the sulphur-sulphur distance has an optimum of around 2.02 Å and a very narrow preferred range of between 2.00 to 2.04 Å. The Cα-Cα distance has an optimum of about 5.8 Å but also greater breadth to its range of about 4.8 to 6.4 Å. Disulphide bonds are also known to not be straight with respect to the Cα and Cβ atoms: The CβSS angle is about 105° whilst the CαCβS angle is about 115°. In one embodiment residues may be selected based on their Cα-Cα distance which is preferably in the range of 2.0 to 10 Å, more preferably in the range of 4.8 to 6.4 Å even more preferably close to the optimum of about 5.8 Å. In another embodiment, pairs outside of the theoretical Cα-Cα distance range may also be considered since it is known both that crystal structures represent a single static conformation of multiple conformation proteins and that all proteins and dimeric proteins and particular polypeptide regions thereof are flexible and mobile and hence may accommodate greater or lesser theoretical Cα-Cα distances. In addition, locations on the cKappa:CH1 interface may also be tested since locations with a very central location are less likely to be solvent exposed.

Preferably the engineered light chain cysteine of cKappa or clambda is introduced at any one of positions 116, 119 or 210 of $C_L$ of human IgG1. Preferably the heavy chain cysteine is introduced at any one of positions 138, 128 or 129 of $C_H1$ of human IgG1. In one embodiment the interchain disulphide bond is between an engineered cysteine at position 116 of $C_L$ and an engineered cysteine at position 138 of $C_H1$. In another embodiment the interchain disulphide bond is between an engineered cysteine at position 119 of $C_L$ and an engineered cysteine at position 128 of $C_H1$. In another embodiment the interchain disulphide bond is between an engineered cysteine at position 210 of $C_L$ and an engineered cysteine at position 129 of $C_H1$.

The present invention also provides useful intermediates for the production of the antibody-effector molecule conjugates of the present invention. Accordingly the present invention also provides an antibody fragment in which the heavy chain ($C_H1$) and light chain ($C_L$) constant regions are linked by an interchain disulphide bond between a pair of engineered cysteines characterized in that the position of the pair of cysteines is selected from position 119 of the light chain and 138 of the heavy chain, position 119 of the light chain and 128 of the heavy chain or position 210 of the light chain and 129 of the heavy chain.

It will be understood by those skilled in the art that due to the high levels of sequence and structural similarity between both human isotypes, kappa and lambda light chains and between species, especially man, mouse, rat, rabbit, hamster, camelids and sharks that similar residue positions can be identified and mutated to cysteine in these antibody sequences.

The antibody fragments of the present invention may be prepared by the use of recombinant DNA techniques involving the manipulation and re-expression of DNA encoding antibody variable and constant regions. Standard molecular biology techniques may be used to modify, add or delete further amino acids or domains as desired. Any alterations to the variable or constant regions are still encompassed by the terms 'variable' and 'constant' regions as used herein. Preferably PCR is used to introduce engineered cysteine residues into the heavy ($C_H1$) and light chain ($C_L$) constant regions. Methods for designing suitable PCR primers are well known in the art and the sequences of antibody $C_H1$ and $C_L$ domains are readily available (Kabat et al., supra). Alternatively cysteines may be introduced using site-directed mutagenesis techniques such as those described in White (Ed.), PCR Protocols: Current Methods and Applications (1993).

The antibody fragment starting material for use in the present invention may be any heavy chain and light chain pair comprising a variable ($V_H/V_L$) and constant region ($C_H/C_L$). Preferably the antibody fragment is a Fab or a Fab' or a truncated Fab fragment as described in WO2005003170.

Fab' fragments for use in the present invention may possess a native or a modified hinge region. The native hinge region is the hinge region normally associated with the $C_H1$ domain of the antibody molecule. A modified hinge region is any hinge that differs in length and/or composition from the native hinge region. Such hinges can include hinge regions from any suitable species, such as human, mouse, rat, rabbit, pig, hamster, camel, llama or goat hinge regions. Other modified hinge regions may comprise a complete hinge region derived from an antibody of a different class or subclass from that of the $C_H1$ domain. Thus, for instance, a $C_H1$ domain of class γ1 may be attached to a hinge region of class γ4. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as alanine, or by converting suitably placed residues into cysteine residues. By such means the number of cysteine residues in the hinge region may be increased or decreased. In addition other characteristics of the hinge can be controlled, such as the distance of the hinge cysteine(s) from the light chain interchain cysteine, the distance between the cysteines of the hinge and the composition of other amino acids in the hinge that may affect properties of the hinge such as flexibility e.g. glycines may be incorporated into the hinge to increase rotational flexibility or prolines may be incorporated to reduce flexibility. Alternatively combinations of charged or hydrophobic residues may be incorporated into the hinge to confer multimerisation properties. Other modified hinge regions may be entirely synthetic and may be designed to possess desired properties such as length, composition and flexibility. A number of modified hinge regions have already been described for example, in U.S. Pat. No. 5,677,425, WO9915549, WO9825971 and WO2005003171 and these are incorporated herein by reference.

The antibody fragment starting material of the present invention may be derived from any antibody isotype including for example IgG, IgM, IgA, IgD and IgE and subclasses thereof including for example IgG1, IgG2, IgG3 and IgG4. Preferably the antibody fragment of the present invention is derived from IgG1. The antibody fragment starting material may be obtained from any species including for example mouse, rat, rabbit, pig, hamster, camel, llama, goat or human. Parts of the antibody fragment may be obtained from more than one species for example the antibody fragments may be chimeric. In one example the constant regions are from one species and the variable regions are from another. In another example the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody.

The recombinant antibody fragments of the present invention, once produced in a host cell may be extracted and purified using any suitable method known in the art. Suitable purification methods include but are not limited to size exclusion, hydrophobic interaction chromatography, protein A, G or L affinity chromatography and ion exchange.

The methods for creating and manufacturing recombinant antibody fragments are well known in the art (see for example, Boss et al., U.S. Pat. No. 4,816,397; Cabilly et al., U.S. Pat. No. 6,331,415; Shrader et al., WO 92/02551; Orlandi et al., 1989, Proc. Natl. Acad. Sci. USA, 86, 3833; Riechmann et al., 1988, Nature, 322, 323; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

The antibody fragment of the present invention will in general be capable of selectively binding to an antigen. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

The term effector molecule as used herein includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Particular antineoplastic agents include cytotoxic and cytostatic agents for example alkylating agents, such as nitrogen mustards (e.g. chlorambucil, melphalan, mechlorethamine, cyclophosphamide, or uracil mustard) and derivatives thereof, triethylenephosphoramide, triethylenethiophosphor-amide, busulphan, or cisplatin; antimetabolites, such as methotrexate, fluorouracil, floxuridine, cytarabine, mercaptopurine, thioguanine, fluoroacetic acid, or fluorocitric acid, antibiotics, such as bleomycins (e.g. bleomycin sulphate), doxorubicin, daunorubicin, mitomycins (e.g. mitomycin C), actionmycins (e.g. dactinomycin) plicamycin, calicheamicin and derivatives thereof, or esperamicin and derivatives thereof; mitotic inhibitors, such as etoposide, vincristine or vinblastine and derivatives thereof; alkaloids such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones, such as mitoxantrone, ureas, such as hydroxyurea; hydrazines, such as procarbazine; or imidazoles, such as dacarbazine.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd, Lu$^{177}$ and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferriox-amine and derivatives thereof.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, albumin, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof.

"Derivatives" as used herein is intended to include reactive derivatives, for example thiol-selective reactive groups such as an α-halocaraboxylic acid or ester, e.g. iodoacetamide, an imide, e.g. maleimide, a vinyl sulphone or disulphide maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 100,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

The polymers of the present invention may be obtained commercially (for example from Nippon Oil and Fats; Nektar Therapeutics) or may be prepared from commercially available starting materials using conventional chemical procedures.

Effector molecules may be attached using standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include for example those described in International Patent Specification numbers WO 93/06231, WO92/22583, WO90/09195, WO89/01476, WO9915549 and WO03031581. Alternatively, where the effector molecule is a protein or polypeptide the linkage may be achieved using recombinant DNA procedures, for example as described in European Patent Specification No. 392745.

The effector molecules may be attached to the antibody fragment of the present invention through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods. See for example U.S. Pat. No. 5,219,996. Preferably effector molecules are covalently linked through a thiol group of a cysteine residue located in the antibody fragment, either naturally or engineered. Suitable natural cysteines for attachment include the interchain cysteines of $C_H1$ and $C_L$ and cysteines in the hinge region as described herein above. The covalent linkage will generally be a disulphide bond, a thioether bond or, in particular, a sulphur-carbon bond. Where a thiol group is used as the point of attachment appropriately activated effector molecules, for example thiol selective derivatives such as such as maleimide, pyridyldithio, vinylsulfone, iodoacetyl, bromoacetyl and cysteine derivatives may be used.

It will be appreciated that where there are two or more effector molecules attached to the antibody fragment these may be identical or different and may be attached to the antibody fragment at different sites. It will also be appreciated that two or more effector molecules may be attached to the antibody fragment at a single site by the use for example of a branched connecting structure to link two or more effector molecules and provide a single site of attachment.

In a preferred aspect of the present invention at least one of the effector molecules attached to the antibody fragment is a polymer molecule, preferably PEG or a derivative thereof. As regards attaching poly(ethyleneglycol) (PEG) moieties in general, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York.

Preferably all the effector molecules attached to the antibody fragment of the present invention are PEG and each molecule is covalently linked via a maleimide group to one or more thiol groups in the antibody fragment. The PEG may be any straight or branched molecule in an average molecular weight range from 500 Da to 100,000 Da, preferably from 5,000 to 40,000 Da and more preferably from 10,000 to 40,000 Da and 20,000 to 40,000 Da. To attach branched PEG molecules, a lysine residue is preferably covalently linked to the maleimide group. To each of the amine groups on the lysine residue is preferably attached a methoxypoly(ethyleneglycol) polymer. In one example the molecular weight of each polymer attached to the lysine is approximately 20,000 Da and the total molecular weight of the entire polymer molecule is therefore approximately 40,000 Da.

Suitable cysteines to which effector molecules may be attached include, where present, the native interchain cysteines, cysteines in the hinge region and other cysteines engineered elsewhere in the antibody fragment, such as the surface.

Particular fragments according to this aspect of the invention include those where:
(i) The antibody fragment is a Fab' fragment and an effector molecule is attached to the hinge.
(ii) The antibody fragment is a Fab' fragment in which the native interchain cysteine of $C_L$ and the native interchain cysteine of $C_H1$ have been replaced by another amino acid, preferably serine, and an effector molecule is attached to the hinge.
(iii) The antibody fragment is a Fab fragment or a truncated Fab fragment in which an effector molecule is attached to each of the native interchain cysteines.
(iv) The antibody fragment is a Fab' fragment and an effector molecule is attached to the native interchain cysteine of $C_L$ and the native interchain cysteine of $C_H1$ and to a cysteine in the hinge region.

The antibody fragment-effector molecule conjugates of the present invention may be produced using any suitable method known in the art. In one embodiment wherein at least one site of effector molecule attachment in the antibody fragment is a cysteine, the cysteine is preferably reduced to produce a free thiol group suitable for effector molecule attachment. The modified antibody fragments according to the invention may therefore be prepared by reacting an antibody fragment as described herein containing at least one reactive cysteine residue with an effector molecule, preferably a thiol-selective activated effector molecule.

Accordingly the present invention further provides a method of producing an antibody fragment to which one or more effector molecules is attached characterized in that the native interchain disulphide bond between the heavy ($C_H1$) and light ($C_L$) chain constant regions is absent and the heavy chain ($C_H1$) and light chain ($C_L$) constant regions are linked by an interchain disulphide bond between a pair of engineered cysteines, one in the light chain constant ($C_L$) region and the other in the heavy chain constant ($C_H1$) region, said method comprising:
a) Treating an antibody fragment in which the heavy chain and light chain constant regions are linked by an interchain disulphide bond between an engineered cysteine in the light chain ($C_L$) and an engineered cysteine in the heavy chain ($C_H1$) constant regions with a reducing agent capable of generating a free thiol group in a cysteine of the heavy and/or light chain constant region and/or, where present, the hinge
b) Reacting the treated fragment with an effector molecule.

Additional effector molecules may be attached elsewhere in the antibody fragment, in particular the constant regions and/or, where present, the hinge. If there are two or more effector molecules to be attached to cysteines in the antibody fragment these may be attached either simultaneously or sequentially by repeating the process. Preferably if two or more effector molecules are attached to cysteines in the antibody fragment they are attached simultaneously.

The method of the present invention also extends to one or more steps before and/or after the reduction method described above in which further effector molecules are attached to the antibody fragment using any suitable method as described previously, for example via other available amino acid side chains such as amino and imino groups.

The reducing agent for use in producing the modified antibody fragments of the present invention is any reducing agent capable of reducing the available cysteines in the antibody fragment of the present invention to produce free thiols for effector molecule attachment. Preferably the reducing agent reduces the native interchain disulphide bond between the interchain cysteine of $C_L$ and the interchain cysteine of $C_H1$, where present, in order to allow attachment of effector molecules to said cysteines. Preferably the reducing agent does not reduce the interchain disulphide bond between the engineered cysteines. It will be clear to a person skilled in the art that suitable reducing agents may be identified by determining the number of free thiols produced after the antibody fragment is treated with the reducing agent. Methods for determining the number of free thiols are well known in the art, see for example Lyons et al., 1990, Protein Engineering, 3, 703. Reducing agents for use in the present invention are widely known in the art for example those described in Singh et al., 1995, Methods in Enzymology, 251, 167-73. Particular examples include thiol based reducing agents such as reduced glutathione (GSH), β-mercaptoethanol (β-ME), β-mercaptoethylamine (β-MA) and dithiothreitol (DTT). Other methods for reducing the antibody fragments of the present invention include using electrolytic methods, such as the method described in Leach et al., 1965, Div. Protein. Chem., 4, 23-27 and using photoreduction methods, such as the method described in Ellison et al., 2000, Biotechniques, 28 (2), 324-326. Preferably however, the reducing agent for use in the present invention is a non-thiol based reducing agent capable of liberating one or more thiols in an antibody fragment. Preferably the non-thiol based reducing agent is capable of liberating the native interchain thiols in an antibody fragment. Preferred reducing agents for use in the present invention are trialkylphosphine reducing agents (Ruegg U T and Rudinger, J., 1977, Methods in Enzymology, 47, 111-126; Burns J et al., 1991, J. Org. Chem., 56, 2648-2650; Getz et al., 1999, Analytical Biochemistry, 273, 73-80; Han and Han, 1994, Analytical Biochemistry, 220, 5-10; Seitz et al., 1999, Euro. J. Nuclear Medicine, 26, 1265-1273; Cline et al., 2004, Biochemistry, 43, 15195-15203), particular examples of which include tris(2-carboxyethyl)phosphine (TCEP), tris butyl phosphine (TBP), tris-(2-cyanoethyl)phosphine, tris-(3-hydroxypropyl)phosphine (THP) and tris-(2-hydroxyethyl) phosphine. Most preferably the reducing agent for use in the present invention is either TCEP or THP. It will be clear to a person skilled in the art that the concentration of reducing agent for use in the present invention can be determined empirically, for example, by varying the concentration of reducing agent and measuring the number of free thiols produced. Typically the reducing agent for use in the present invention is used in excess over the antibody fragment for example between 2 and 1000 fold molar excess. Preferably the reducing agent is in 2, 3, 4, 5, 10, 100 or 1000 fold excess. In one embodiment the reductant is used at between 2 and 5 mM.

The reactions in steps (a) and (b) of the method described above may generally be performed in a solvent, for example an aqueous buffer solution such as acetate or phosphate, at around neutral pH, for example around pH 4.5 to around pH 8.5, typically pH 4.5 to 8, suitably pH6 to 7. The reaction may generally be performed at any suitable temperature, for example between about 5° C. and about 70° C., for example at room temperature. The solvent may optionally contain a chelating agent such as EDTA, EGTA, CDTA or DTPA. Preferably the solvent contains EDTA at between 1 and 5 mM, preferably 2 mM. Alternatively or in addition the solvent may be a chelating buffer such as citric acid, oxalic acid, folic acid, bicine, tricine, tris or ADA. The effector molecule will generally be employed in excess concentration relative to the concentration of the antibody fragment. Typically the effector molecule is in between 2 and 100 fold molar excess, preferably 5, 10 or 50 fold excess.

Where necessary, the desired product containing the desired number of effector molecules and retaining the interchain disulphide between the engineered cysteines may be separated from any starting materials or other product generated during the process of attaching an effector molecule by conventional means, for example by chromatography techniques such as ion exchange, size exclusion, protein A, G or L affinity chromatography or hydrophobic interaction chromatography. Accordingly the method of the present invention may optionally further comprise an additional step, (c), in which the antibody fragment to which one or more effector molecules is attached and in which the engineered interchain disulphide is retained is purified.

The antibody fragments according to the invention may be useful in the detection or treatment of a number of diseases or disorders. Such diseases or disorders may include those described under the general heading of infectious disease, e.g. bacterial infection; fungal infection; inflammatory disease/autoimmunity e.g. rheumatoid arthritis, osteoarthritis, inflammatory bowel disease; cancer; allergic/atopic disease e.g. asthma, eczema; congenital disease, e.g. cystic fibrosis, sickle cell anemia; dermatologic disease e.g. psoriasis; neurologic disease, e.g. multiple sclerosis; transplants e.g. organ transplant rejection, graft-versus-host disease; and metabolic/idiopathic disease e.g. diabetes.

The antibody fragments according to the invention may be formulated for use in therapy and/or diagnosis and according to a further aspect of the invention we provide a pharmaceutical composition comprising an antibody fragment to which one or more effector molecules is attached characterized in that the native interchain disulphide bond between the heavy ($C_H1$) and light ($C_L$) chain constant regions is absent and the heavy chain ($C_H1$) and light chain ($C_L$) constant regions are linked by an interchain disulphide bond between a pair of engineered cysteines, one in the light chain constant ($C_L$) region and the other in the heavy chain constant ($C_H1$) region together with one or more pharmaceutically acceptable excipients, diluents or carriers.

EXAMPLES

The present invention will now be described by way of example only.

The aim was to identify pairs of engineered cysteines that can be shown to form a disulphide bond by the use of non reducing SDS-PAGE and immunoblotting. Cysteine pairs were identified using a single crystal structure of a human cKappa:CH1 interface. The aim was to find residues that had a Cα-Cα distance close to the optimum of about 5.8 Å, but residues within the range of about 2.0 to about 10 Å were also identified. Pairs outside of the theoretical Cα-Cα distance range were also considered since it is known both that crystal structures represent a single static conformation of multiple conformation proteins and that all proteins and dimeric proteins and particular polypeptide regions thereof are flexible and mobile and hence may accommodate greater or lesser theoretical Cα-Cα distances. In addition a range of locations on the cKappa:CH1 interface were tested since locations with a very central location are less likely to be solvent exposed. A single humanised Fab' framework (g165) was used throughout as a model Fab' protein. Three control constructs were used to aid SDS-PAGE comparisons:

i) a wild type γ1 Fab' designated LC-C HC-C, hinge-CAA which contains the native interchain disulphide cysteines and a single hinge thiol. This protein runs as a ~50 kDa band during non-reduced SDS-PAGE and can offer 1, 2 or 3 (generally 1 or 3) cysteines for effector molecule attachment upon reduction depending upon the conditions used.

ii) a 'Δ-inter' γ1 Fab' designated LC-S HC-S, hinge-CAA in which the native interchain disulphide cysteines have been mutated to Serine whilst retaining a single hinge thiol. This protein runs as two 25 kDa bands on non-reduced SDS-PAGE and provides only 1 cysteine for effector molecule attachment upon reduction.

iii) a 'dog-tail' γ1 Fab' designated LC-C HC-S, hinge-CAA in which the heavy chain native interchain cysteine has been mutated to Serine whilst the native interchain cysteine of the light chain and a single hinge thiol are retained. 'Dog-tail' Fab' have been observed to efficiently form an interchain disulphide bond between cKappa and the hinge and so is also observed as a ~50 kDa band during non-reduced SDS-PAGE and can provide 2 cysteines for effector molecule attachment upon reduction.

Fab' molecules were produced in *E. coli* and purified using standard methods (see for example, Humphreys et al., 2002, Protein Expression and Purification, 26, 309-320). PCR mutagenesis was used to change the interchain cysteines of $C_L$ and $C_H1$ to serines and to introduce cysteine encoding codons at other sites in the antibody fragments.

Example 1

Formation of Engineered Interchain Disulphide Bonds in g165 LC-S HC-S, Hinge-CAA Fab' and g165 LC-S HC-S, Hinge-SAA Fab'

Cysteine encoding codons were introduced using standard recombinant DNA techniques into a 'Δ-inter' 71 g165 Fab' (LC-S HC-S, hinge-CAA). Since the light chain (LC) and heavy chain (HC) of 'Δ-inter' γ1 g165 Fab' are non-covalently associated, the formation of a new disulphide bond could be simply analysed by running Fab' samples on non-reducing SDS-PAGE and by immunoblotting detection with anti-cKappa and anti-$C_H1$ reagents. Three cysteine pairs identified as useful by small-scale expression and SDS-PAGE analysis were expressed at larger scale to permit purification and test reduction and modification. In addition, since it is known that the thiol containing hinge region is highly flexible and could possibly form a disulphide bond with an engineered cKappa cysteine these four variants were also constructed in a Fab' with a null hinge i.e. designated LC-S HC-S, hinge-SAA. Hence any disulphide bond formed in these 'hinge-SAA' variants could only have been due to the introduced cKappa and $C_H1$ mutations.

Cysteine pairs 1 to 7 were identified by the analysis of a human cKappa:$C_H1$ crystal structure. Pair 8 was to introduce the $C_H1$ cysteine in the location found to be a cysteine in IgM, IgG2, 3 and 4 to make a 'pseudo γ4 Fab'. Similar mutations have been made previously: both converting an IgG1 to be 'IgG4 like' (Dorai et al., Mol. Immunol. 1992 29:1487-1491) and conversely changing an IgG3 to be 'IgG1 like' (Brekke et al., 1993. Mol. Immunol. 30:1419-1425). The amino acids changed and their Kabat numbers are shown in Table 1. The plasmids produced are shown in Table 2.

TABLE 1

Amino acids mutated.

| Kabat notation (kappa:CH1) | Cα-Cα distance (Å) (4D5 crystal) | Cysteine pair i.d. |
|---|---|---|
| F116C:A138C | 8.73 | Pair 1 |
| P119C:A125C | 6.4 | Pair 2 |
| P119C:S128C | 6.4 | Pair 3 |
| F209C:S128C | 5.74 | Pair 4 |
| F209C:K129C | 5.89 | Pair 5 |
| N210C:K129C | 7.71 | Pair 6 |
| F116C:A139C | 5.96 | Pair 7 |
| C214C:S127C | 12.65 | Pair 8 |

TABLE 2

Plasmids

| Plasmid | Fab' details | Kappa mut. | CH1 mut. | Cysteine pair i.d. |
|---|---|---|---|---|
| pDPH147 | g165 Fab' LC-C HC-C, hinge-CAA | — | — | classic Fab' |
| pDPH197 | g165 Fab' LC-S HC-S, hinge-CAA | — | — | Δ-inter Fab' |
| pDPH225 | g165 Fab' LC-C HC-S, hinge-CAA | — | — | dog-tail Fab' |
| pDPH295 | g165 Fab' LC-S HC-S, hinge-CAA | F116C | A138C | Pair 1 |
| pDPH296 | g165 Fab' LC-S HC-S, hinge-CAA | P119C | A125C | Pair 2 |
| pDPH297 | g165 Fab' LC-S HC-S, hinge-CAA | P119C | S128C | Pair 3 |
| pDPH298 | g165 Fab' LC-S HC-S, hinge-CAA | F209C | S128C | Pair 4 |
| pDPH299 | g165 Fab' LC-S HC-S, hinge-CAA | F209C | K129C | Pair 5 |
| pDPH300 | g165 Fab' LC-S HC-S, hinge-CAA | N210C | K129C | Pair 6 |
| pDPH306 | g165 Fab' LC-S HC-S, hinge-CAA | F116C | A139C | Pair 7 |
| pDPH329 | g165 Fab' LC-C HC-S, hinge-CAA | wt (C214C) | S127C | Pair 8-pseudo γ4 |
| pDPH330 | g165 Fab' LC-C HC-S, hinge-SAA | wt (C214C) | S127C | Pair 8 |
| pDPH331 | g165 Fab' LC-S HC-S, hinge-SAA | F116C | A138C | Pair 1 |
| pDPH332 | g165 Fab' LC-S HC-S, hinge-SAA | P119C | S128C | Pair 3 |
| pDPH333 | g165 Fab' LC-S HC-S, hinge-SAA | N210C | K129C | Pair 6 |

Immunoblots of non-reduced SDS-PAGE of periplasmic extracts of *E. coli* small scale expressions of g165 LC-S HC-S, hinge-CAA Fab' with introduced pairs of cKappa:$C_H1$ cysteines were detected with anti-Kappa and anti-$C_H1$ reagents. All of the introduced cysteine pairs were observed to form some covalently linked cKappa-$C_H1$ (Fab') protein with the same mobility as a purified Fab' standard. Increased proteolysis was observed with some of the constructs suggesting that the introduced disulphide caused changes to the rate of folding or physical stability of the Fab' in the periplasm. Three constructs were observed as having the best balance of disulphide formation, yield and minimal proteolysis: pDPH295 g165 Fab' LC-S HC-S, hinge-CAA F116C: A138C, pDPH297 g165 Fab' LC-S HC-S, hinge-CAA P119C:S128C and pDPH300 g165 Fab' LC-S HC-S, hinge-CAA N210C:K129C.

Immunoblots of non-reduced SDS-PAGE of periplasmic extracts of *E. coli* small scale expressions of g165 LC-S HC-S, hinge-SAA Fab' with introduced pairs of cKappa:$C_H1$ cysteines were also detected with anti-Kappa and anti-$C_H1$ reagents. Mutation of the hinge cysteine to serine removes any possibility of disulphide formation between cKappa and the hinge or blocking of the $C_H1$ cysteine by the hinge cysteine. Disulphide bonding was still observed as evidenced by the presence of the ~50 kDa Fab band when detected with an anti-$C_H1$ reagent. Detection using an anti-cKappa reagent showed some differences, in particular the disappearance of a high molecular weight band of a doublet in Pair 6 upon mutation of the hinge to −SAA which suggests that the N210C cKappa mutation found in Pair 6 is partially available for disulphide formation with the hinge cysteine.

Example 2

Thermal Stability of g165 LC-S HC-S, Hinge-CAA Fab' and In Vivo Disulphide Formation Periplasmic extractions of fermentation cell pellets were agitated overnight at 30° C., 50° C., or 65° C. in the presence or absence of 10 mM NEM before analysis by SDS-PAGE and immunoblotting. Immunoblots of non-reduced SDS-PAGE of periplasmic extracts of *E. coli* fermentations expressing g165 LC-S HC-S, hinge-CAA Fab' with introduced pairs of cKappa:$C_H1$ cysteines (Pairs 1, 3 and 6) were detected with an anti-CH1 reagent. For the three mutants tested (Pairs 1, 3 and 6) all were found to be stable with overnight incubations up to 65° C. demonstrating both that the ~50 kDa band was formed by a stable disulphide bond and that the mutations had not radically destabilised the overall Fab structure. Inclusion of 10 mM N-ethyl maleimide (NEM) which irreversibly blocks free thiols in the overnight temperature extraction did not affect the amount or stability of disulphide formed. This suggests that the vast proportion of LC-HC disulphide formation had occurred prior to the extraction, most probably in vivo in the *E. coli* periplasm.

Further evidence for the thermal stability conferred by the presence of an intact interchain disulphide bond is shown in Table 3. Fab' was extracted from *E. coli* fermentations at 30° C. and 55° C. and purified by ProteinG chromatography. Between 55 and 100% of the Fab produced was able to withstand the higher temperature overnight incubation suggesting that there was an intact disulphide bond present in this proportion of the periplasmic Fab'.

TABLE 3

Purification of g165 Fab' from *E. coli* fermentations.

| Plasmid | Fab type | Fab' yield, 30° C. extraction | Fab' yield, 55° C. extraction | 55° C./ 30° C. |
|---|---|---|---|---|
| pDPH295 | g165 Fab' LC-S HC-S, hinge-CAA F116C:A138C | 32.3 mg/l | 26.3 mg/l | 81% |
| pDPH297 | g165 Fab' LC-S HC-S, hinge-CAA P119C:S128C | 68.5 mg/l | 38.0 mg/l | 55% |
| pDPH300 | g165 Fab' LC-S HC-S, hinge-CAA N210C:K129C | 65.1 mg/l | 65.1 mg/l | 100% |
| pDPH329 | g165 Fab' LC-C HC-S, hinge-CAA C214C:S127C | — | 104 mg/l | — |

Example 3

Formation of Interchain Disulphide Bonds in g165 'Pseudo γ4' Fab'

IgG1 is unique amongst antibody structures in that they use a $C_H1$ cysteine in the upper hinge (Kabat #233) to bond to the light chain whereas all others such as IgG4 use a cysteine more N-terminal in the $C_H1$ sequence (Kabat #127). To make Pair 8 the $C_H1$ cysteine of a γ1 Fab was mutated to serine (C233S) and then the compensating S127C mutation was made. In a γ1 Fab' crystal structure the calculated Cα-Cα distance is 12.65 Å well beyond the normal range for disulphide bond formation. In contrast the Cα-Cα distance for the native γ1 cKappa-$C_H1$ disulphide is 5.32 Å. Non-reducing SDS-PAGE gels showed that in spite of these observations LC-HC disulphide bond formation was quite efficient between these two cysteines at these positions. Comparison of hinge-CAA and hinge-SAA variants suggested that there is no involvement of the hinge cysteine in this disulphide bond. Some LC dimer was also observed.

These observations suggest that the C-terminus of cKappa is mobile and flexible enough to reduce some of the 12.65 Å span to a more credible 5-7 Å.

Example 4

Modification of Antibody Fragments Containing Engineered Cysteine Pairs with a Cysteine Reactive Effector Molecule Using Strong and Weak Reductants PEG-maleimide is a suitable test reagent to demonstrate the solvent accessibility of the novel cysteine pairs. The addition of significant extra molecular mass such as a 20 kDa PEG is easily detected using SDS-PAGE. Disulphide bonds that are deeply buried within or between protein domains will not be accessible to solvent-borne reductants.

The effect of reduction with 5 mM β-MA at room temperature for one hour in 0.1M phosphate 2 mM EDTA pH6.0 buffer was tested. All Fab' were at 1.4 mg/ml during the reduction, and reductant was removed using a PD10 desalting column after which the Fab' concentration was approximately 0.8 mg/ml. 20 kDa PEG-maleimide was added at 5× excess (mg/mg) resulting in an approximately 6 M excess. Non-reducing SDS-PAGE was used to analyse the resulting fragments. Covalently associated polypeptides run as a ~50 kDa band unless modified by the addition of multiples of 20 kDa PEG chains. Non covalently associated polypeptides such as those found in the Δ-inter control construct or where a disulphide bond has been reduced will migrate as separate 25 kDa bands. The control fragments behaved as expected following mild β-MA reduction and PEGylation. The inter-chain disulphide bond found in the 'dog-tail' Fab' was largely intact after the reduction and PEGylation however a small percentage of 'dog-tail' Fab' was reduced to LC and HC and these were each PEGylated. The Δ-inter control Fab' was mono-PEGylated on the hinge as expected. The classic Fab' control was also monoPEGylated on the hinge and the native interchain disulphide remained intact. All three of the new engineered disulphide pairings were able to withstand the mild β-MA reduction and Fab' with an intact engineered interchain disulphide that was monoPEGylated at the hinge was produced. The purified protein preparations of pDPH297 (Pair 3) and pDPH300 (Pair 6) also contained some non-covalently associated LC and HC some of which was also PEGylated. Such material can readily be purified away from the desired modified Fab' fragment using standard methods in the art such as size exclusion chromatography.

Stronger reducing conditions were also tested, this time using 10 mM TCEP as the reductant (all other conditions remained the same). Non-reducing SDS-PAGE showed that the classic Fab' behaved as expected with the majority of this protein being substantially reduced and PEGylated to result in monoPEGylated LC and diPEGylated HC. Reduction and PEGylation of the engineered antibody fragments encoded by pDPH295 (pair 1), pDPH297 (pair 3) and pDPH300 (pair 6) produced a Fab' with an intact interchain disulphide that was monoPEGylated at the hinge. This is further evidence that these disulphide pairs have an improved occlusion from the aqueous environment. A proportion of both unPEGylated free heavy and light chains and PEGylated free heavy and light chains was also observed. Such material can readily be purified away from the desired modified Fab' fragment using standard methods in the art such as size exclusion chromatography.

Example 5

Effect of Novel Disulphide Bonds on Antigen Binding Affinity

The antigen binding affinity of Fab' fragments can be affected by subtle structural perturbations. The binding affinity for the antigen of g165 Fab' was unaffected by the protein engineering involved in making pairs 1, 3 and 6.

The invention claimed is:

1. An antibody fragment having a heavy chain constant region ($C_H1$) and a light chain constant region ($C_L$), one or more effector molecules being attached to said fragment, said fragment characterized in that the native interchain disulphide bond between native interchain cysteines in the heavy ($C_H1$) and light ($C_L$) chain constant regions is absent and the heavy chain ($C_H1$) and light chain ($C_L$) constant regions are linked by an interchain disulphide bond between a pair of engineered cysteines, one in the light chain constant ($C_L$) region and the other in the heavy chain constant ($C_H1$) region, wherein the position of the pair of engineered cysteines is selected form position 116 of the light chain and 138 of the heavy chain, position 119 of the light chain and 128 of the heavy chain or position 210 of the light chain and 129 of the heavy chain, said positions as defined by the Kabat numbering system for IgG1.

2. An antibody fragment according to claim 1 in which at least one effector molecule is attached to a cysteine in the antibody fragment.

3. An antibody fragment having a heavy chain constant region ($C_H1$) and a light chain constant region ($C_L$), said fragment characterized in that the native interchain disulphide bond between native interchain cysteines in the heavy ($C_H1$) and light ($C_L$) chain constant regions is absent, in which the heavy chain ($C_H1$) and light chain ($C_L$) constant regions are linked by an interchain disulphide bond between a pair of engineered cysteines characterized in that the position of the pair of cysteines is selected from position 116 of the light chain and 138 of the heavy chain, position 119 of the light chain and 128 of the heavy chain or position 210 of the light chain and 129 of the heavy chain, said positions as defined by the Kabat numbering system for IgG1.

4. The antibody fragment according to claim 1 in which the antibody fragment is a Fab or Fab'.

5. The antibody fragment according to claim 1 wherein the native interchain cysteines have been replaced by another amino acid.

6. The antibody fragment according to claim 5 in which the native interchain cysteines have been replaced by serine.

7. The antibody fragment according to claim 1 in which the antibody fragment is a Fab' and an effector molecule is attached to a cysteine in the hinge region.

8. The antibody fragment according to claim 1 in which an effector molecule is attached to each of the interchain cysteines.

9. The antibody fragment according to claim 1 in which the effector molecule is PEG.

10. The antibody fragment according to claim 3 in which the antibody fragment is a Fab or Fab'.

11. The antibody fragment according to claim 3 wherein the native interchain cysteines have been replaced by another amino acid.

12. The antibody fragment according to claim 11 in which the native interchain cysteines have been replaced by serine.

* * * * *